US006917831B2

(12) United States Patent
Bloemer et al.

(10) Patent No.: US 6,917,831 B2
(45) Date of Patent: Jul. 12, 2005

(54) ELECTRICALLY ACTIVATED IMPLANT

(75) Inventors: Frank Bloemer, Berlin (DE); Max Schaldach, deceased, late of Erlangen (DE); by Max Schaldach, Jr., legal representative, Berlin (DE)

(73) Assignee: BIOTRONIK Mess- und Therpiegeraete GmbH & Co. Ingenieurbuero Berlin, Berlin (DE)

( * ) Notice: Subject to any disclaimer, the term of this patent is extended or adjusted under 35 U.S.C. 154(b) by 428 days.

(21) Appl. No.: 09/963,109

(22) Filed: Sep. 25, 2001

(65) Prior Publication Data

US 2002/0068956 A1 Jun. 6, 2002

(30) Foreign Application Priority Data

Sep. 28, 2000  (DE) .......................................... 100 49 727

(51) Int. Cl.⁷ .............................................. A61N 1/362
(52) U.S. Cl. ...................................................... 607/16
(58) Field of Search ............................. 607/16, 30–32, 607/59, 60, 1

(56) References Cited

U.S. PATENT DOCUMENTS

| 5,080,096 | A | | 1/1992 | Hooper | |
| 5,342,408 | A | * | 8/1994 | deCoriolis et al. | 607/32 |
| 5,350,407 | A | * | 9/1994 | McClure et al. | 607/16 |
| 5,370,666 | A | * | 12/1994 | Lindberg et al. | 607/16 |
| 5,414,405 | A | | 5/1995 | Hogg | |
| 5,425,361 | A | | 6/1995 | Fenzlein | |
| 5,522,856 | A | * | 6/1996 | Reineman | 607/9 |
| 6,016,448 | A | * | 1/2000 | Busacker et al. | 607/29 |
| 6,285,897 | B1 | | 9/2001 | Kilcoyne | |
| 6,689,056 | B1 | * | 2/2004 | Kilcoyne et al. | 600/300 |

FOREIGN PATENT DOCUMENTS

| DE | 197 58 393 A1 | 7/1999 |
| EP | 0 545 242 A1 | 11/1992 |
| EP | 0 560 470 A1 | 9/1993 |
| FR | 2 781 905 A1 | 2/2000 |
| WO | WO 95/16313 A1 | 6/1995 |
| WO | WO 00/59376 A1 | 10/2000 |
| WO | WO 01/35813 A1 | 5/2001 |

* cited by examiner

Primary Examiner—George R. Evanisko
(74) Attorney, Agent, or Firm—Hahn Loeser + Parks LLP

(57) ABSTRACT

This invention relates to an electrically active implant with a plurality of energy-consuming components and an activation device designed to activate the implant. The electrically active implant is characterized by a deactivation device designed to deactivate the energy-consuming components of the implant, where the energy-consuming components of the implant can be deactivated during the implant's storage by means of the deactivation device, and, furthermore, characterized by a device for permanent storage of the implant-specific data.

18 Claims, 2 Drawing Sheets

ELECTRICALLY ACTIVATED IMPLANT

The present invention relates to an electrically active implant comprising energy-consuming components and activation devices to activate the implant.

BACKGROUND OF THE ART

After the manufacturing of an implant such as a pacemaker or a defibrillator, and before its implantation the implant is usually stored. The typical energy consumption of a pacemaker held in storage is about 8 µA as opposed to about 12 to 22 µA after its implantation, depending on the programming and the degree of inhibition. It follows from these facts that two years of storage equal about one year of implantation. The energy consumed during the storage can, therefore, no longer be used during the implantation period so that the effective utilization time of the implant, i.e., the implantation time, is reduced.

The current "Use before" date, that is, the date by which the implant must be put in operation, depends on the date when the battery was connected, the date of sterilization, a product-specific time period, and it also takes into account the energy consumption during the storage. After the expiration of the "Use before" date, the devices that have not been implanted in the meantime are sent back to the manufacturer for a re-sterilization. In this process it can happen that such devices can no longer be delivered back as merchantable products due to the loss of charge during their storage. As a matter of fact, there is no substantial reason—except for the condition of the battery—that would enforce a maximum "Use before" period of, e.g., 24 months. The "Use before" time period could be extended by reducing the quantity of the current consumed during the storage, which could reduce the number of implants to be returned for re-sterilization as well as the number of implants to be scrapped.

The function of pacemakers and especially of defibrillators is dependent on the temperature. If during the storage or transportation the temperature is, e.g., below 5° C., there might occur mostly reversible but also irreversible defects. Units damaged in such a manner can usually no longer be supplied as normal products, since the current consumption after the defect and, therefore, the condition of the battery can no longer be determined with sufficient accuracy.

The current state of art knows electrical implants that are partially set into an energy-saving stand-by operation mode during their storage. In this process, certain components of the implant are usually disconnected, while other components continue to be supplied with current. The purpose of this energy-saving stand-by operation mode is to reduce the consumption of current during the storage.

U.S. Pat. No. 5,522,856 discloses an implant, which sets selected circuit elements of the implant into an energy-saving operation mode until the implant is implanted in a patient. This known implant further comprises a detector, which determines, whether the implant is being connected for the implantation. When such an implantation is detected, the circuit elements of the implant are switched into normal current-consuming operation mode. Furthermore, the implant can be removed from the storage, its function can be tested, and then the implant can be returned into the storage, where the implant is again switched into the energy-saving stand-by mode in order to reduce the current consumption during the storage. In addition, the implant can detect when the impedance at its electrodes is under a certain pre-set level. If this is the case, the implant remains permanently in normal operation mode.

U.S. Pat. No. 5,350,407 discloses an implant that can be put into a stand-by mode by means of an instruction from an external communication device, and can be put into an active mode by removing an activation pin, or by an activation instruction from external communication device. After the manufacturing of the implant an activation pin is introduced into the implant and the external communication device is triggered to transmit a deactivation instruction to the implant. In doing so, the energy supply to a section of the circuit components is disconnected, while energy supply is kept open to those circuit elements, which are required—in conjunction with the communication operation—to activate the remaining circuit elements. The implant is then activated either by the transmission of an activation instruction from an external communication device or by removing the activation pin.

As a consequence, the two aforementioned documents already disclose a reduction of current consumption of the implant during its storage. However, it is desirable to reduce the current consumption of the implant during its storage even more.

Therefore, the task of this invention is to further develop the design of an electrically active implant in such a manner as to further reduce the current consumption of the implant during its storage as compared to the current state of the art.

SUMMARY OF THE INVENTION

This task is resolved by an electrically active implant according to claim 1.

The underlying idea of this invention is to design an electrically active implant with energy-consuming components and activation devices to activate the implant. Furthermore, the electrically active implant comprises deactivation devices to deactivate the energy-consuming components of the implant, where the energy-consuming components of the implant can be deactivated during the implant's storage by means of the deactivation devices. In addition, the implant comprises a device for permanent storage of implant-specific data.

The advantages of this invention consist primarily in the fact that during the storage of the implant all its energy-consuming components can be deactivated or disconnected so that no current flows in the implant during its storage. Furthermore, it is ensured that all necessary implant-specific data are maintained even when all energy-consuming components of the implant are disconnected.

One design version of this invention comprises a permanent electronic memory, into which implant-specific data are entered after the manufacturing of the implant. The data stored in this permanent electronic memory can be retrieved without any problem after the implant has been activated.

In another design version of the invention, the memory device comprises a bar code displayed on the implant, which contains the implant-specific data. Here too, the implant-specific data can be retrieved after the activation of the implant. As an alternative, the bar code containing the implant-specific data can be displayed on the packaging of the implant.

In one design version of the invention, the activation device comprises at least one switch that can be activated in a wireless manner, where such switch serves the purpose of re-activating the deactivated energy-consuming components. This switch can be activated in a magnetic or telemetric manner. Using the wireless-operated switch, the reactivation can be performed without any physical intervention in the implant.

In another design version of the invention, the bar code located on the implant or on the packaging of the implant is read by an external bar code scanner, whereby the implant-specific data are retrieved and sent to the implant by means of an external telemetric transmitter. The implant-specific data transmitted to the implant are stored in a memory of the implant. In this manner, the implant-specific data can be stored in the implant also afterwards.

One design version of the invention comprises an implant with a switch that can be magnetically activated, and a packaging with a magnet, which is arranged in such a manner that the magnetically activated switch of the implant is activated whenever the implant is being removed from the packaging. This makes possible an automatic activation of the implant while it is being removed from the packaging to be implanted.

In another design version of the invention, the implant comprises a reactivation-blocking device to block repeated activation or deactivation of the energy-consuming components of the implant. This feature is to prevent repeated unauthorized activation and deactivation of the implant.

Additional design versions of this invention are the subject of the subclaims.

BRIEF DESCRIPTION OF THE DRAWINGS

The present invention will be best understood when reference is made to the accompanying drawings, where identical parts are identified by identical reference numerals and wherein.

DETAILED DESCRIPTION OF THE PREFERRED EMBODIMENT

Figure 1:
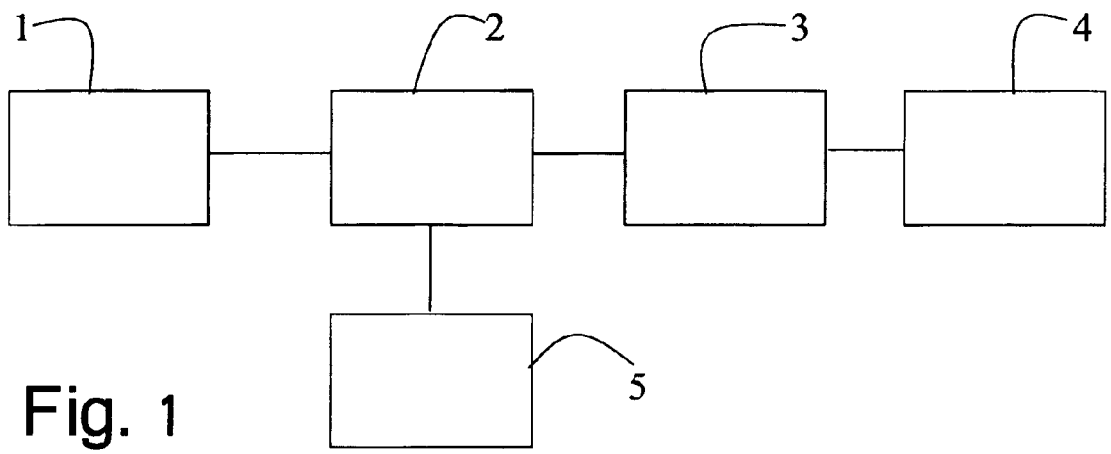
FIG. 1 shows a schematic block diagram of an implant according to the first design example.

FIG. 1 shows the first design example of an electrically active implant. The implant comprises a battery 1, activation/deactivation device 2, a reactivation blocking device 5, which is connected with activation/deactivation device 2, a plurality of conventional energy-consuming components 3 of the implant, and a permanent electronic memory 4.

After the manufacturing of the implant, implant-specific data such as the serial number of the implant and the factory program are stored in permanent electronic memory 4. The data stored in memory 4 are maintained even after current supply is disconnected so that they can be used again after the implant is activated.

After the implant has been checked by the final quality assurance test, all of the plurality of current-consuming components such 3 as the CPU, charge pumps, output units, etc. are deactivated, i.e., disconnected. Such implants are then stored in this current-less condition. This process makes possible that the current consumption of an implant is substantially reduced during its storage and is actually near the zero level.

The current-less storage of the implant allows extending the implantation time, i.e., the time during which the implant is implanted in the body.

Furthermore, the temperature influence during the storage or the transportation of the implant can be almost eliminated due to the deactivation of the current-consuming components.

When the stored implant is to be implanted in a body or when it is already implanted, an activation of the plurality of energy-consuming components 3 occurs. The activation occurs by means of a small magnet located in a blister pack, which activates a REED switch located in the implant. When the implant is removed from the blister pack, the REED switch closes and activates, e.g., the pacemaker function. In this function or rather operation mode, the implant works in its normal operation mode. In other words, energy-consuming components 3 of the implant are supplied with current by battery 1 so that the implant can perform all functions and access the implant-specific data stored in memory 4.

In order to prevent a subsequent deactivation—after the activation has been performed—by opening the REED switch through a subsequent application of a magnet, the implant comprises a reactivation-blocking device 5. This reactivation-blocking device 5 controls the circuits of the implant in such a manner that a reactivation by the user is excluded and is made possible only by the parameter-setting person using a special telemetric transmitter.

Figure 2:
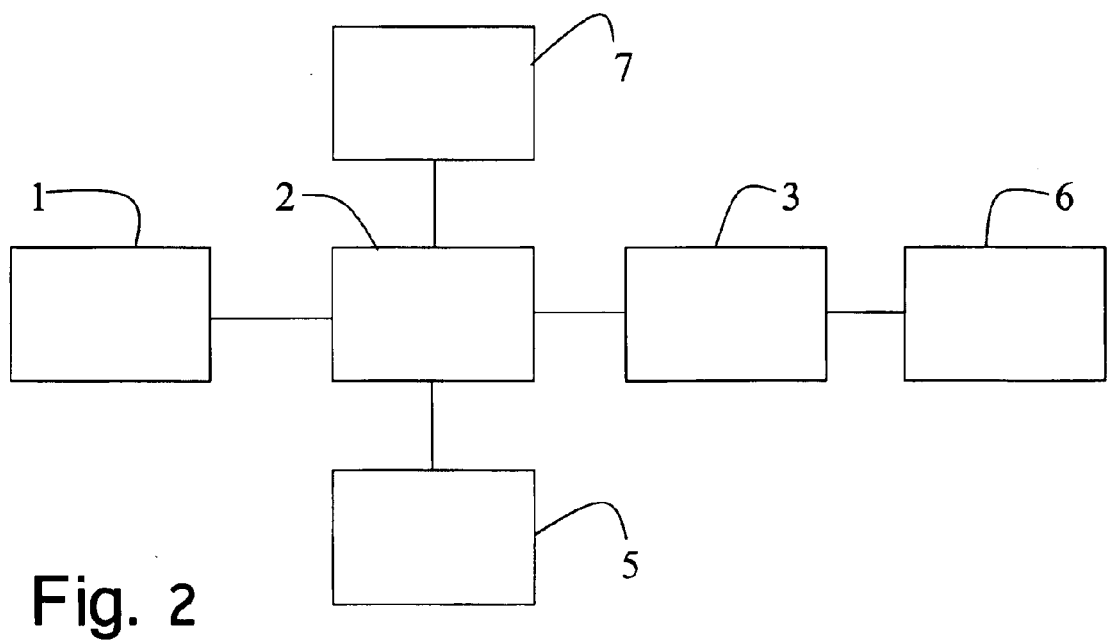
FIG. 2 shows a schematic block diagram of an implant according to the second design example.
Figure 3:
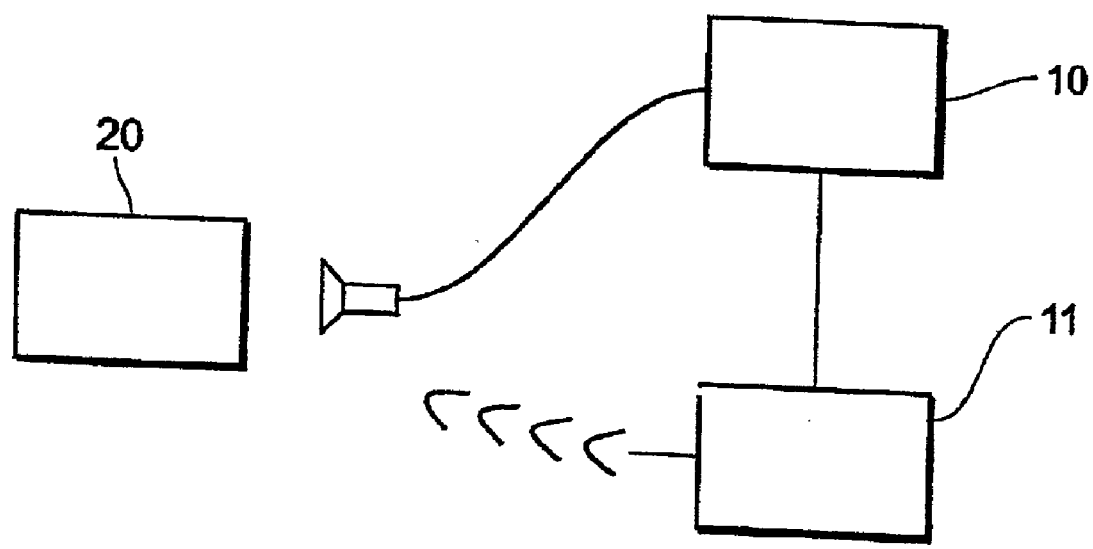
FIG. 3 shows the combined effect and coordination of the components of the second design example.

FIGS. 2 and 3 show an implant according to a second design example (FIG. 2) and the coordination of its components (FIG. 3). The implant comprises a battery 1, an activation/deactivation device 2, a plurality of energy-consuming components, designated generally as 3, a reactivation-blocking device 5, and a memory 6. In this design example, no data are stored in the implant after the factory quality assurance test. The implant is completely switched off so that it consumes no energy during its storage.

The implant-specific data are encoded and converted into a bar code. This bar code is then placed on the implant or on its packaging.

After the implant is manufactured and packed, it is possible—by a corresponding telemetric command—to separate battery 1 from the energy-consuming components 3 of the implant by means of activation/deactivation device 2.

Before delivery of the implant to the final customer the implant is initiated by means of a programming device. As shown by FIG. 3, this external programming device 12 comprises a bar code scanner 10 and a telemetric transmitter 11. The bar code scanner reads the bar code located on the implant or on its packaging, retrieves the implant-specific data and sends these data telemetrically to the implant, where these data are stored in memory 6 for further use. The information transmitted by transmitter 11 are received by a receiver 7 of the implant and forwarded to memory 6, where they are stored.

The reading of the bar code and the transmission of the retrieved implant-specific data should occur as follows:

1. Reading of bar code data
2. Retrieving of implant-specific data
3. Transmitting the data to the implant
4. Reverse transmitting the data stored in the implant
5. Comparing the transmitted and returned data
6. Confirming the correct initialization if the transmitted and returned data are correct.

During steps 1 to 6 the bar code is permanently scanned. If a change occurs (e.g., the bar code is removed), the initialization process is immediately interrupted without confirmation.

This feature is meant to prevent the case that the scanned data of one implant are stored in another implant.

The activation of the implant after delivery occurs similarly as in the design example in FIG. 1 by the application of a magnet, which closes a REED switch, whereby the plurality of energy-consuming components 3 of the implant are connected to battery 1 in order to be supplied with current and voltage.

After a complete initialization of the implant the REED switch is permanently by-passed, e.g., by means of a thermoelement. The thermoelement can be designed as a bimetallic release. The permanent by-pass allows eliminating a false deactivation in the implanted state.

Of course, such permanent by-pass of the REED switch can be incorporated also in the first design example.

As an alternative to the first and second design examples the initial factory program and serial number can be stored in a separate memory of the implant, which is continually supplied with voltage. All other energy-consuming components of the implant such as CPU, charge pumps, output units and the like are completely deactivated, i.e., disconnected after the final factory quality ensurance test.

During the storage of the implant only the memory for the initial factory program and the serial number consumes current, whereas all other components of the implant are disconnected.

There exist several possibilities for the activation of the implant before its implantation. As shown in the first design example, a REED switch located inside the implant is activated by means of a magnet located in the blister. When the implants is being removed from the blister, the REED switch closes and thus activated the normal operation mode of the implant by connecting the energy-consuming components to the battery, whereby they are supplied with current and voltage. A reactivation-blocking device prevents a deactivation of the implant by opening the REED switch through the application of a magnet.

Furthermore, the activation can be performed by means of a pin in the implant. The removal of this pin or plug before the implantation causes that the ventricular different contact in the implant is connected, for a short time and with low impedance, with the indifferent contact. This signal is used by the control electronics of the implant to permanently activate the full functionality of the implant.

In addition, the activation can occur in such a manner that a lying electrode is connected to the implant. The electronics of the implant record an external load, which is less then 3200 Ohm, whereby the full functionality is permanently activated.

What is claimed is:

1. An electrically active implant, said implant comprising:
   a plurality of energy-consuming components;
   at least one wirelessly activated switch, connected to at least one of said plurality of energy-consuming components, for activating and deactivating at least one of said plurality of energy-consuming components;
   a storage device connected to said implant for permanently storing implant-specific data; and
   a blocking means, connected to said at least one wirelessly activated switch, for blocking repeated reactivation of at least one of said plurality of energy-consuming components.

2. The implant of claim 1 wherein said at least one wirelessly activated switch is activated magnetically.

3. The implant of claim 1 wherein said at least one wirelessly activated switch is activated telemetrically.

4. The implant of claim 1 further comprising packaging for the implant, wherein the packaging includes a magnet to activate the at least one wirelessly activated switch when the implant is removed from the packaging.

5. The implant of claim 1 wherein the storage device comprises a bar code located on the implant, the bar code containing the implant-specific data.

6. The implant of claim 5 further comprising a second memory connected to the plurality of components, wherein the implant is adapted to receive the implant specific data by an external telemetric transmitter and store the data in said second memory.

7. The implant of claim 1, further comprising a packaging capsule, and wherein
   the implant is encased in the packaging capsule, and wherein
   the storage device comprises a bar code located on the packaging capsule, the bar code containing the implant-specific data.

8. The implant of claim 7 further comprising a second memory connected to the plurality of components, wherein the implant is adapted to receive the implant specific data by an external telemetric transmitter and store the data in said second memory.

9. An electrically active implant, said implant comprising:
   a plurality of energy-consuming components;
   at least one telemetrically activated switch, connected to at least one of said plurality of energy-consuming components, for activating and deactivating at least one of said plurality of energy-consuming components;
   a storage device connected to said implant for permanently storing implant-specific data; and
   a blocking means, connected to said at least one telemetrically activated switch, for blocking repeated reactivation of at least one of said plurality of energy-consuming components.

10. The implant of claim 9 wherein the storage device comprises a bar code located on the implant, the bar code containing the implant-specific data.

11. The implant of claim 10, further comprising a second memory connected to the plurality of components, wherein the implant is adapted to receive the implant specific data by an external telemetric transmitter and store the data in said second memory.

12. The implant of claim 9, further comprising a packaging capsule, and wherein
    the implant is encased in the packaging capsule, and wherein
    the storage device comprises a bar code located on the packaging capsule, the bar code containing the implant-specific data.

13. The implant of claim 12 further comprising a second memory connected to the plurality of components, wherein the implant is adapted to receive the implant specific data by an external telemetric transmitter and store the data in said second memory.

14. An electrically active implant, said implant comprising:
    a plurality of energy-consuming components;
    at least one wirelessly activated switch, connected to at least one of said plurality of energy-consuming components, for activating and deactivating at least one of said plurality of energy-consuming components;
    a permanent electronic memory, electrically connected to at least one of said energy-consuming components, for permanently storing implant-specific data; and
    a blocking means, connected to said at least one wirelessly activated switch, for blocking repeated reactivation of at least one of said plurality of energy-consuming components.

15. The implant of claim 14 wherein said at least one wirelessly activated switch is activated magnetically.

16. The implant of claim 14 wherein said at least one wirelessly activated switch is activated telemetrically.

17. The implant of claim 14 further comprising packaging for the implant, wherein the packaging includes a magnet to activate the at least one wirelessly activated switch when the implant is removed from the packaging.

18. An electrically active implant, said implant comprising:
- a plurality of energy-consuming components;
- at least one telemetrically activated switch, connected to at least one of said plurality of energy-consuming components, for activating and deactivating at least one of said plurality of energy-consuming components;
- a permanent electronic memory, electrically connected to at least one of said energy-consuming components, for permanently storing implant-specific data; and
- a blocking means, connected to said at least one telemetrically activated switch, for blocking repeated reactivation of at least one of said plurality of energy-consuming components.

* * * * *